(12) United States Patent
Deshpande et al.

(10) Patent No.: US 10,788,970 B2
(45) Date of Patent: Sep. 29, 2020

(54) EFFICIENT DETERMINATION OF MR SCAN PARAMETERS

(71) Applicant: Siemens Healthcare GmbH, Erlangen (DE)

(72) Inventors: Vibhas S. Deshpande, Austin, TX (US); Peter Kollasch, Minnetonka, MN (US); Dingxin Wang, Apple Valley, MN (US)

(73) Assignee: Siemens Healthcare GmbH, Erlangen (DE)

( * ) Notice: Subject to any disclaimer, the term of this patent is extended or adjusted under 35 U.S.C. 154(b) by 256 days.

(21) Appl. No.: 15/187,877

(22) Filed: Jun. 21, 2016

(65) Prior Publication Data

US 2017/0364252 A1    Dec. 21, 2017

(51) Int. Cl.
*A61B 5/055*    (2006.01)
*G06F 3/0484*    (2013.01)

(52) U.S. Cl.
CPC .......... *G06F 3/04847* (2013.01); *A61B 5/055* (2013.01)

(58) Field of Classification Search
CPC .... G06F 3/04847; G06F 3/0412; A61B 5/055
See application file for complete search history.

(56) References Cited

U.S. PATENT DOCUMENTS

| 2004/0024303 | A1* | 2/2004 | Banks | A61B 5/7435 |
| | | | | 600/407 |
| 2010/0052680 | A1* | 3/2010 | Wohlfarth | A61B 5/055 |
| | | | | 324/309 |
| 2015/0022203 | A1* | 1/2015 | Gumbrecht | G01R 33/5659 |
| | | | | 324/309 |
| 2016/0077179 | A1* | 3/2016 | Tomoda | G01R 33/543 |
| | | | | 324/314 |
| 2017/0185280 | A1* | 6/2017 | Kim | G01R 33/546 |

FOREIGN PATENT DOCUMENTS

KR    101788742 B1 * 12/2015

* cited by examiner

*Primary Examiner* — Seth A Silverman

(57) ABSTRACT

A system comprises presentation of a user interface on the display for inputting a first set of parameter values for a magnetic resonance scan, reception of the first set of parameter values for the magnetic resonance scan from a user via the displayed user interface, and automatic determination, based on the first set of parameter values, of first additional parameter values for the magnetic resonance scan.

19 Claims, 7 Drawing Sheets

EFFICIENT DETERMINATION OF MR SCAN PARAMETERS

BACKGROUND

An MR scanner generates images of patient anatomy based on sequences of RF pulses. The RF pulses, their sequences and the generation of images are governed by MR scan parameters. The MR scan parameters must be selected so as to produce images which are suitable for their intended clinical purposes.

Selection of appropriate MR scan parameters for a given clinical scenario is complicated from a user perspective. New MR scanning techniques are being introduced regularly, which further increases this complexity. Moreover, MR scanner hardware and software (e.g., field strength, system type, bore size, gradient systems, receive coils, available parameters, etc.), differ from system-to-system and from vendor-to-vendor. These factors may contribute to inefficient and/or incorrect selection of MR scan parameters, which may subsequently lead to sub-optimal imaging.

BRIEF DESCRIPTION OF THE DRAWINGS

FIG. 3 is an outward view of a user interface for specifying clinical scan parameters according to some embodiments.

FIG. 4 is an outward view of a user interface for specifying clinical scan parameters according to some embodiments.

DETAILED DESCRIPTION

The following description is provided to enable any person in the art to make and use the described embodiments. Various modifications, however, will remain readily apparent to those in the art.

Generally, some embodiments facilitate efficient determination of MR scan parameters. According to some embodiments, a user specifies values of a reduced parameter set and remaining MR scan parameters are determined therefrom. The reduced parameter set may comprise parameters which are primarily clinically-related (e.g., target, tissue contrast, image resolution, coverage, imaging time, etc.).

Figure 1:
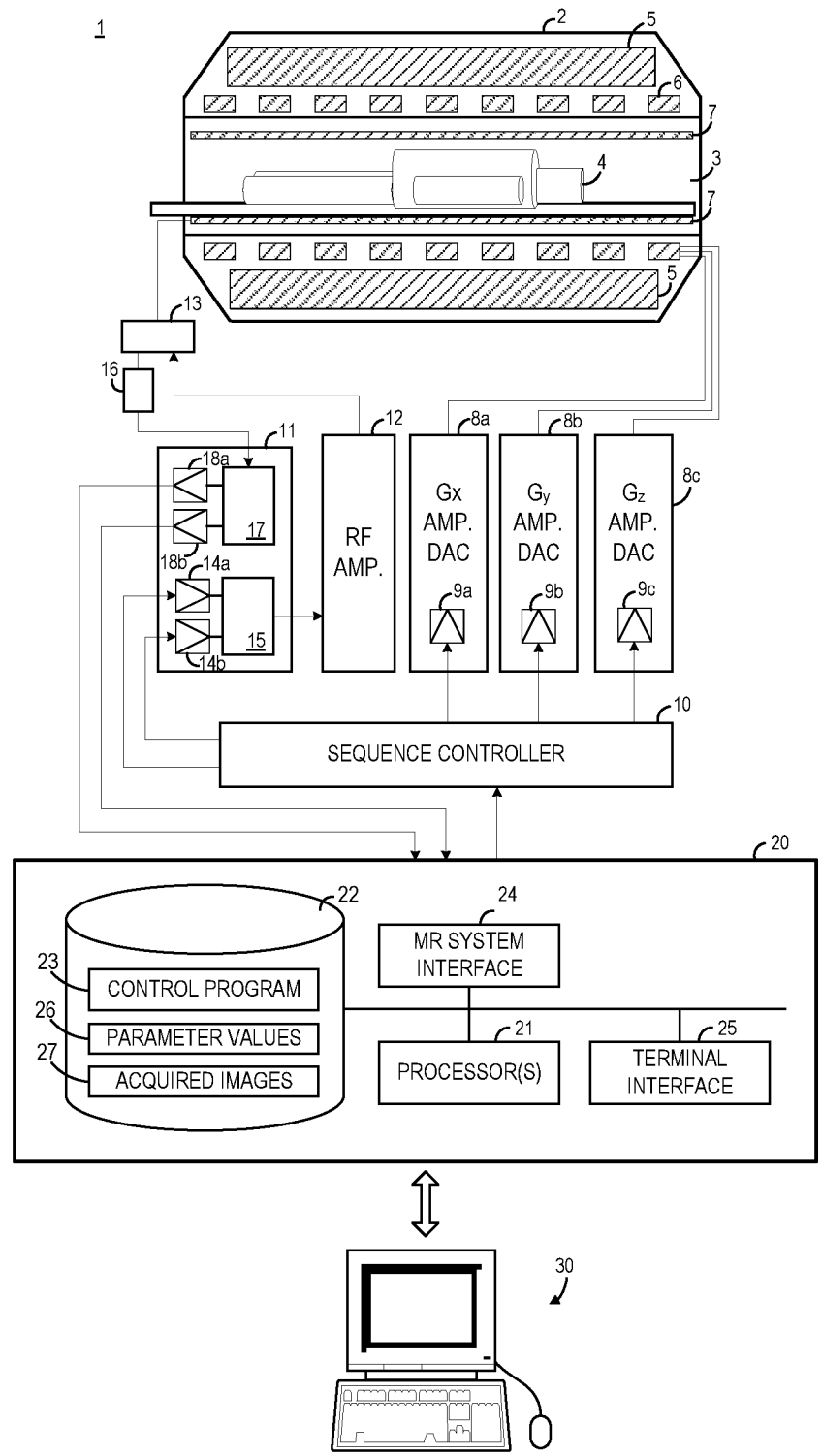
FIG. 1 is a block diagram of an MRI system according to some embodiments.

FIG. 1 illustrates MR system 1 according to some embodiments. MR system 1 includes MR chassis 2, which defines bore 3 in which patient 4 is disposed. MR chassis 2 includes polarizing main magnet 5, gradient coils 6 and RF coil 7 arranged about bore 3. According to some embodiments, polarizing main magnet 5 generates a uniform main magnetic field ($B_0$) and RF coil 7 emits an excitation field ($B_1$).

According to MR techniques, a substance (e.g., human tissue) is subjected to a main polarizing magnetic field (i.e., $B_0$), causing the individual magnetic moments of the nuclear spins in the substance to process about the polarizing field in random order at their characteristic Larmor frequency, in an attempt to align with the field. A net magnetic moment $M_z$ is produced in the direction of the polarizing field, and the randomly-oriented magnetic components in the perpendicular plane (the x-y plane) cancel out one another.

The substance is then subjected to an excitation field (i.e., $B_1$) created by emission of a radiofrequency (RF) pulse, which is in the x-y plane and near the Larmor frequency, causing the net aligned magnetic moment $M_z$ to rotate into the x-y plane so as to produce a net transverse magnetic moment $M_t$, which is rotating, or spinning, in the x-y plane at the Larmor frequency. The excitation field is terminated and signals are emitted by the excited spins as they return to their pre-excitation field state. The emitted signals are detected, digitized and processed to reconstruct an image using one of many well-known MR reconstruction techniques.

An RF pulse may be emitted as a magnetization preparation step in order to enhance or suppress signals from certain tissue so as to generate desired levels of contrast in the resulting image. For example, an inversion, or saturation, pulse is used in non-contrast-enhanced angiography to suppress venous blood in order to highlight the arterial system.

Gradient coils 6 produce magnetic field gradients $G_x$, $G_y$, and $G_z$ which are used for position-encoding NMR signals. The magnetic field gradients $G_x$, $G_y$, and $G_z$ distort the main magnetic field in a predictable way so that the Larmor frequency of nuclei within the main magnetic field varies as a function of position. Accordingly, an excitation field $B_1$ which is near a particular Larmor frequency will tip the net aligned moment $M_z$ of those nuclei located at field positions which correspond to the particular Larmor frequency, and signals will be emitted only by those nuclei after the excitation field $B_1$ is terminated.

Gradient coils 6 may consist of three windings, for example, each of which is supplied with current by an amplifier 8a-8c in order to generate a linear gradient field in its respective Cartesian direction (i.e., x, y, or z). Each amplifier 8a-8c includes a digital-analog converter 9a-9c which is controlled by a sequence controller 10 to generate desired gradient pulses at proper times.

Sequence controller 10 also controls the generation of RF pulses by RF system 11 and RF power amplifier 12. RF system 11 and RF power amplifier 12 are responsive to a scan prescription and direction from sequence controller 10 to produce RF pulses of the desired frequency, phase, and pulse amplitude waveform. The generated RF pulses may be applied to the whole of RF coil 7 or to one or more local coils or coil arrays. RF coil 7 converts the RF pulses emitted by RF power amplifier 12, via multiplexer 13, into a magnetic alternating field in order to excite the nuclei and align the nuclear spins of the object to be examined or the region of the object to be examined. As mentioned above, RF pulses may be emitted in a magnetization preparation step in order to enhance or suppress certain signals.

The RF pulses are represented digitally as complex numbers. Sequence controller 10 supplies these numbers in real and imaginary parts to digital-analog converters 14a-14b in RF system 11 to create corresponding analog pulse sequences. Transmission channel 15 modulates the pulse sequences with a radio-frequency carrier signal having a base frequency corresponding to the resonance frequency of the nuclear spins in the volume to be imaged.

RF coil 7 both emits radio-frequency pulses as described above and scans the alternating field which is produced as a result of processing nuclear spins, i.e. the nuclear spin echo signals. The received signals are received by multiplexer 13, amplified by RF amplifier 16 and demodulated in receiving channel 17 of RF system 11 in a phase-sensitive manner. Analog-digital converters 18a and 18b convert the demodulated signals into a real part and an imaginary part.

Computing system 20 receives the real and imaginary parts and reconstructs an image therefrom according to known techniques. System 20 may comprise any general-purpose or dedicated computing system. Accordingly, system 20 includes one or more processing units 21 (e.g., processors, processor cores, execution threads, etc.) configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of control program 23. One or more processing units 21 may execute control program 23 to cause system 20 to perform any one or more of the processes described herein. For example, one or more processing units 21 may execute control program 23 to cause system 20 to receive MR scan parameter values from a user, and to determine remaining MR scan parameter values based thereon. Such values may be stored in parameter values 26, and may be subsequently used to perform a corresponding MR scan.

In this regard, one or more processing units 21 may execute control program 23 to provide instructions to sequence controller 10 via MR system interface 24. For example, sequence controller 10 may be instructed to initiate an MR pulse sequence based on a set of parameter values 26 which was received and determined as described herein. In particular, sequence controller 10 may be instructed to control the switching of magnetic field gradients via amplifiers 8a-8c at appropriate times, the transmission of radio-frequency pulses having a specified phase and amplitude at specified times via RF system 11 and RF amplifier 12, the reception of real and imaginary parts of a resulting RF signal via MR system interface 24, and the reconstruction of an image therefrom. Such an image may be stored among acquired images 28 of storage device 22.

Acquired images 27 may be provided to terminal 30 via terminal interface 25 of system 20 for viewing by a user. Terminal interface 25 may also receive input from terminal 30, which may be used to provide commands to control program 23 in order to control sequence controller 10 and/or other elements of system 1. The commands may specify MR scan parameter values which are used by system 20. Terminal 30 may comprise a display device and an input device coupled to system 20. In some embodiments, terminal 30 is a separate computing device such as, but not limited to, a desktop computer, a laptop computer, a tablet computer, and a smartphone.

Each element of system 1 may include other elements which are necessary for the operation thereof, as well as additional elements for providing functions other than those described herein. Storage device 22 may also store data and other program code for providing additional functionality and/or which are necessary for operation of system 20, such as device drivers, operating system files, etc.

Figure 2:
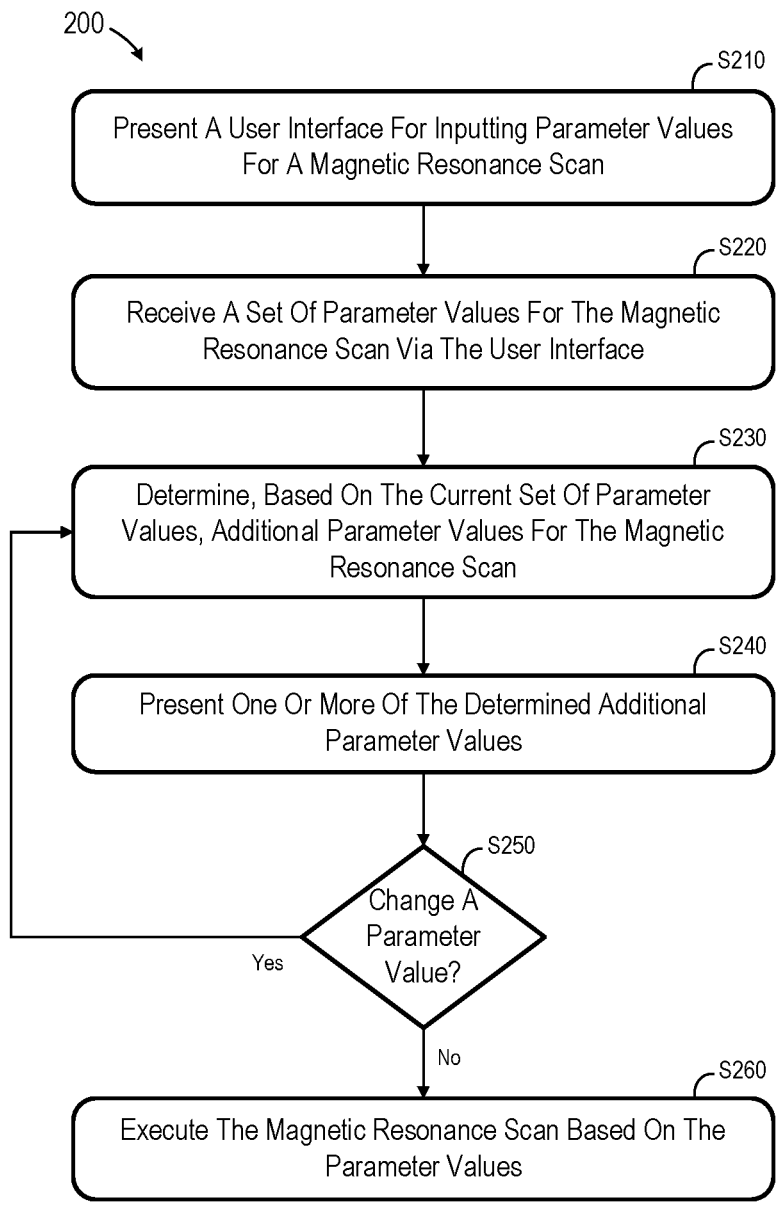
FIG. 2 is a flow diagram of a process according to some embodiments.

FIG. 2 comprises a flowchart of process 200 according to some embodiments. In some embodiments, various hardware elements of system 1 (e.g., one or more processors) execute program code to perform process 200. Process 200 and all other processes mentioned herein may be embodied in processor-executable program code read from one or more of non-transitory computer-readable media, such as a floppy disk, a disk-based or solid-state hard drive, CD-ROM, a DVD-ROM, a Flash drive, and a magnetic tape, and then stored in a compressed, uncompiled and/or encrypted format. In some embodiments, hard-wired circuitry may be used in place of, or in combination with, program code for implementation of processes according to some embodiments. Embodiments are therefore not limited to any specific combination of hardware and software.

Figures 3, 4:
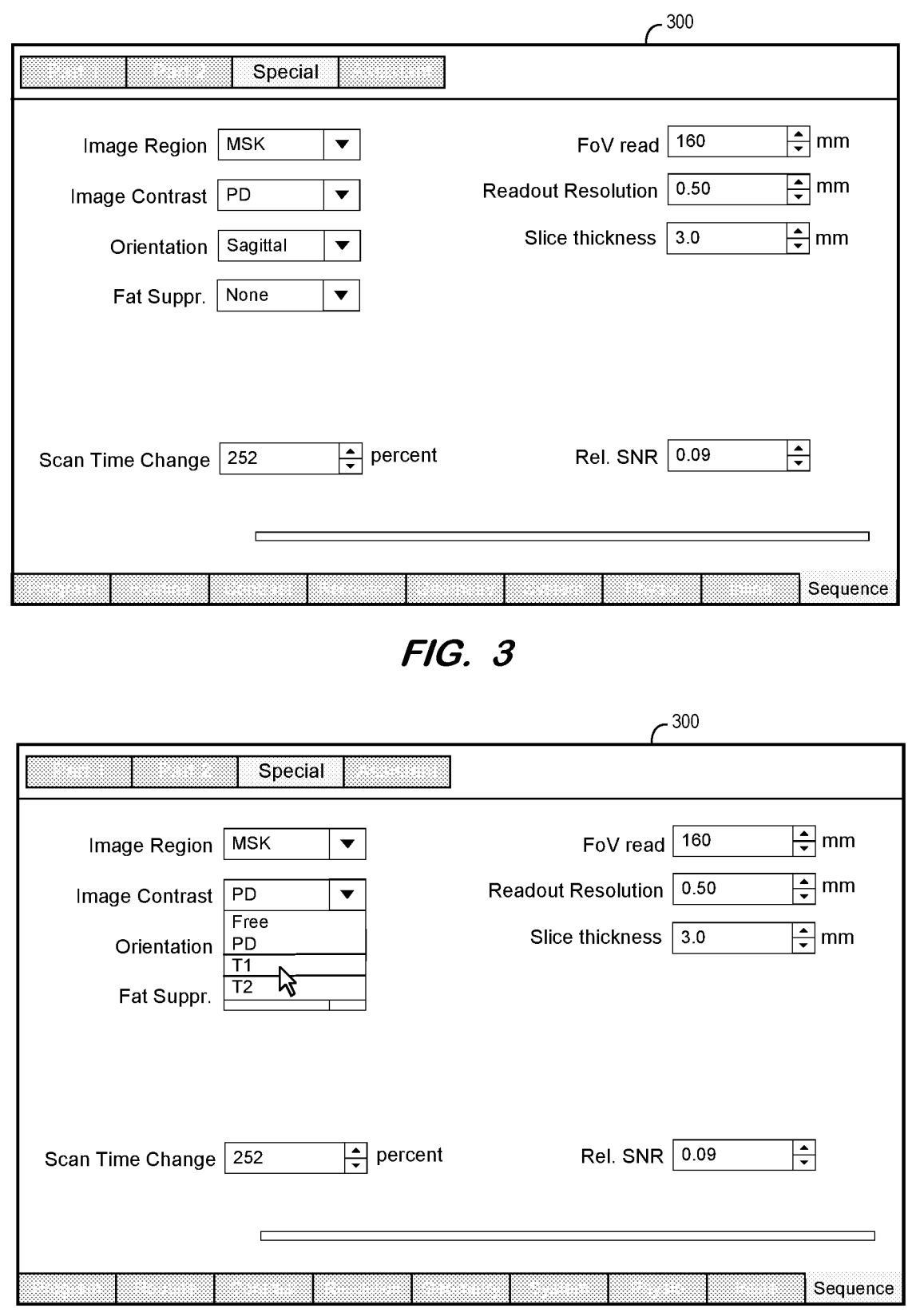

A user interface is presented at S210. The user interface may comprise a user interface for inputting parameter values for an MR scan. FIG. 3 illustrates UI 300 which may be displayed at S210 according to some embodiments. UI 300 may be presented to an operator on terminal 30 via execution of control program 23. Embodiments are not limited to UI display and manipulation on terminal 30. For example, UI 300 and the other UIs described herein may be presented on a handheld device such as a tablet computer, with user interaction therewith being transmitted to terminal 30 and/or to computing system 20.

UI 300 presents nine fields for specifying nine parameter values of an MR scan. Embodiments are not limited to these parameter values, and may provide for user specification of more or fewer parameter values. According to some embodiments, the presented user interface allows input of values for a manageable and clinically-oriented subset of MR scan parameters. Such clinically-oriented parameters may include one or more of, but are not limited to, region, contrast, fat suppression, field-of-view, resolution and slice thickness.

The user interface presented at S210 may comprise any layout, format and/or UI controls which are or become known, including but not limited to slider controls, touch-screen interfaces, etc. The user interface may allow input of MR scan parameter values which are not clinically-oriented. In some instances, user input of some MR scan parameter values is required while user input of other MR scan parameter values is optional.

Next, at S220, a set of parameter values for the MR scan is received via the user interface. In one example of S220, the user has input parameter values into the presented user interface using terminal 30 at S210 and these parameter values are received by system 20. Additional parameter values for the MR scan are determined at S230 based on the received set of parameter values. System parameters are derived from knowledge of the system hardware and sensors, and any system-connected elements such as coils.

As an example of some embodiments, it is assumed that user interface 300 of FIG. 3 is presented at S210, including previously-determined parameter values of a stored MR scan. Next, as shown in FIG. 4, the user changes the Image Contrast parameter value from "PD" to "T1" and this change is received at S220. Additional parameter values for the MR scan are determined at S230 based on the received set of parameter values (i.e., all parameter values shown in user interface 300, including the changed value). The additional parameter values determined at S230 are values sufficient to define a complete MR scan for one application. The values may be determined using known algorithms which take into account factors including, but not limited to, system hardware and software configurations, MR physics and application knowledge, patient information, previously-acquired patient images, learned behavior of system usage, etc. In the case of the example, the determined parameter values include values which differ from corresponding previously-determined values of the stored MR scan.

Figures 5, 6:
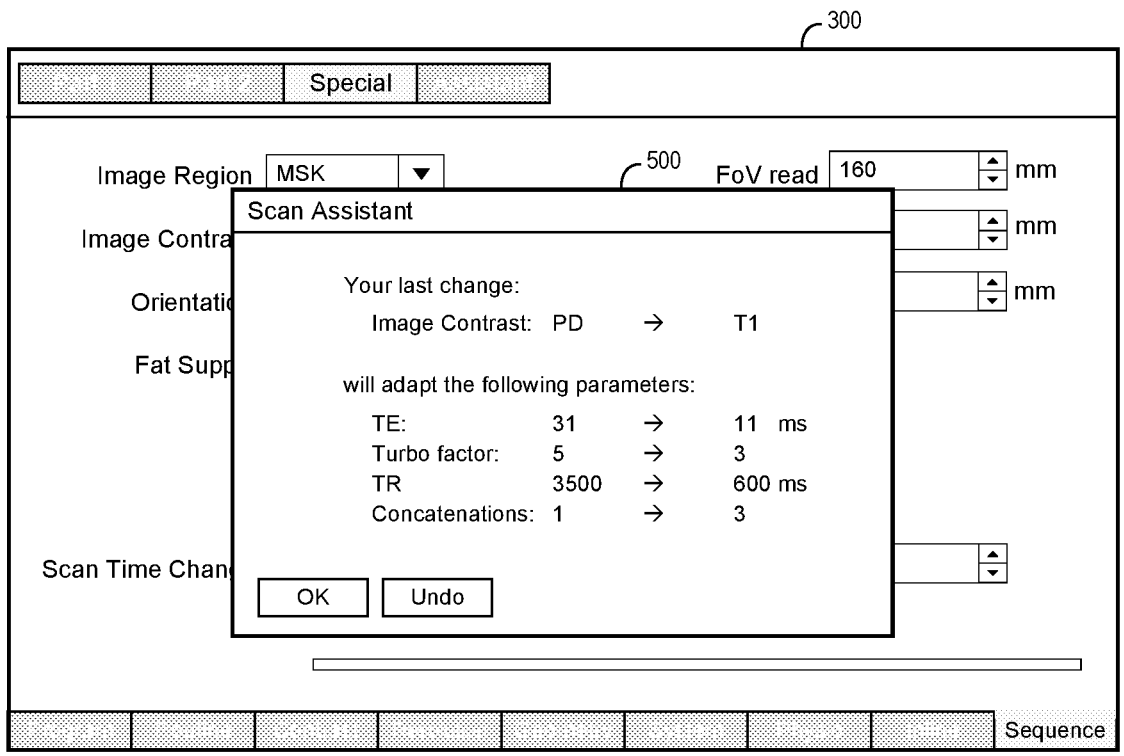
FIG. 5 is an outward view of a user interface for presenting scan parameter changes determined according to some embodiments.
FIG. 6 is an outward view of a user interface for presenting scan parameters according to some embodiments.

The one or more determined additional parameter values are presented at S240. According to some embodiments, these determined values are presented to the user using dialog 500 of FIG. 5. Dialog 500 indicates to the user that the change to the Image Contrast parameter value results in changes to values of four parameters, as compared to the values of those parameters in the stored MR scan.

Upon selecting "OK" control of dialog 500, the user is also presented with user interface 600 at S240, including one or more of the changed values, as well as other of the determined additional parameter values. According to some embodiments, each parameter value shown in user interface 600 (and possibly others) was determined at S230 based on the parameter values received at S220. Embodiments are not limited to the parameters described herein. Generally, some embodiments may involve receiving any predetermined subset of required MR scan parameter values at S220, with the remaining required parameter values being determined at S230.

Figure 7:
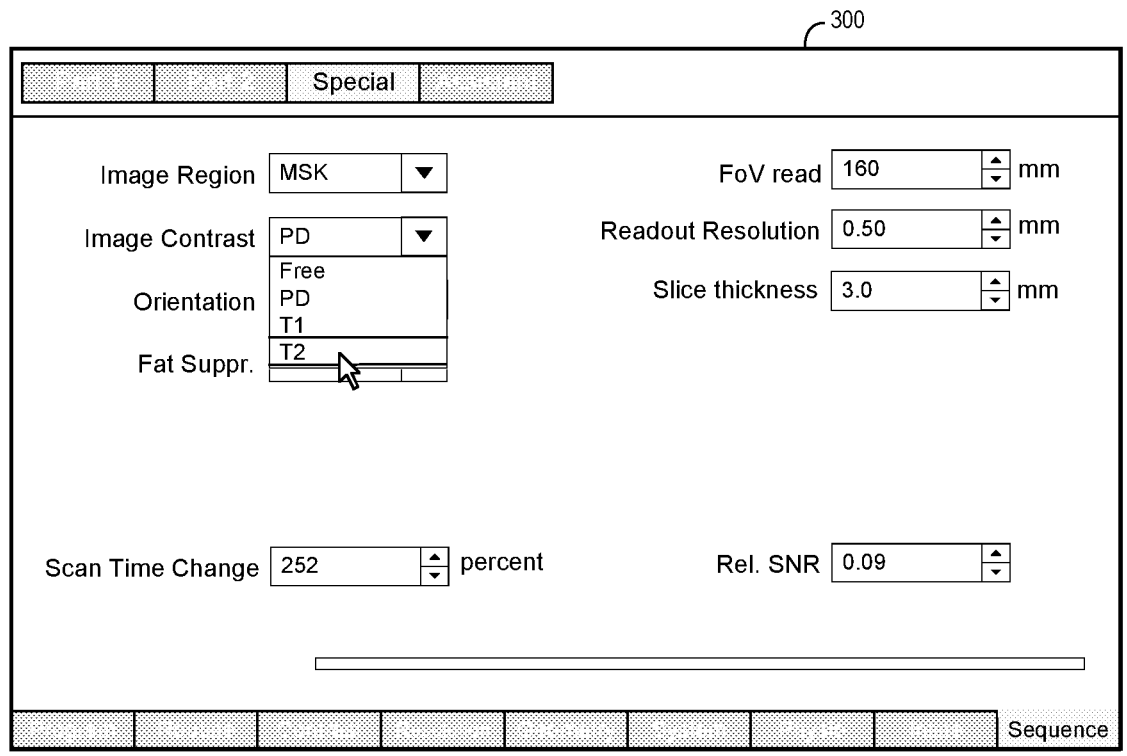
FIG. 7 is an outward view of a user interface for specifying clinical scan parameters according to some embodiments.
Figure 8:
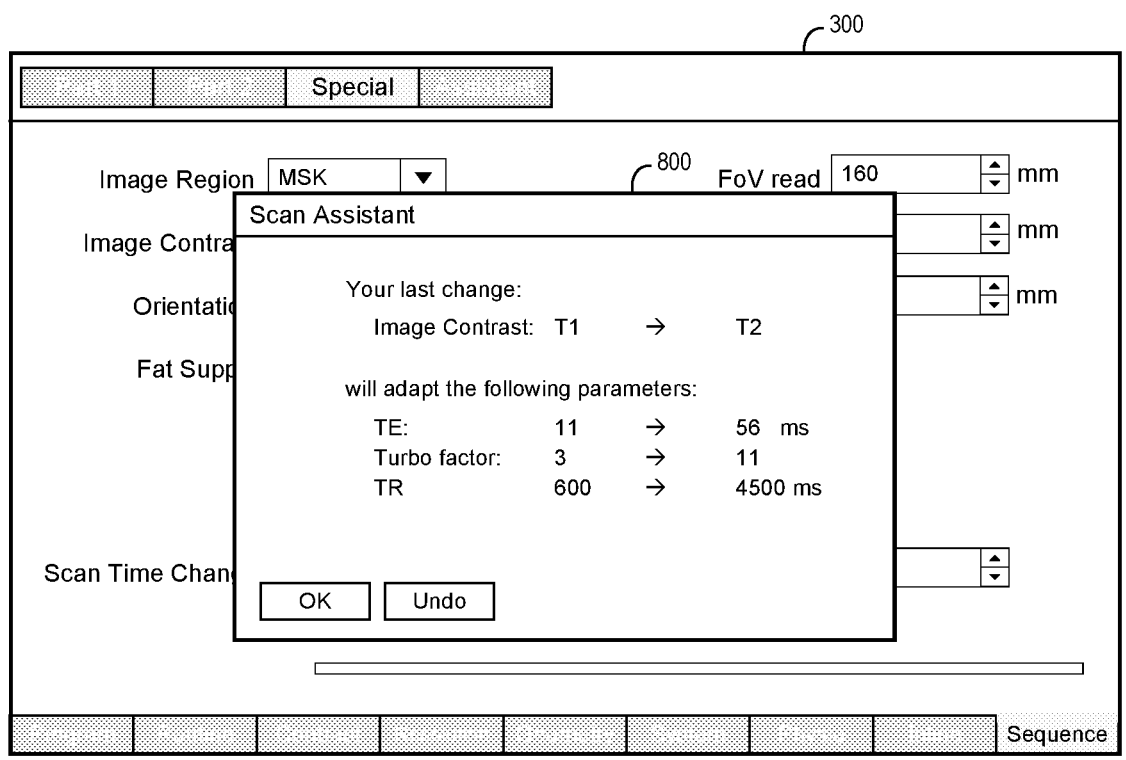
FIG. 8 is an outward view of a user interface for presenting scan parameter changes determined according to some embodiments.
Figure 9:
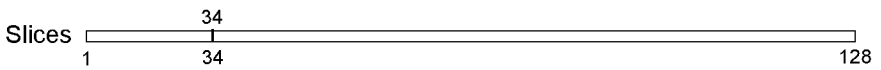
FIG. 9 is an outward view of a user interface for presenting scan parameters according to some embodiments.

At S250, it is determined whether the user has changed a parameter value of the MR scan. For example, as shown in FIG. 7, the user may further manipulate user interface 300 to change the now-current value of the parameter Image Contrast from "PD" to "T2". Accordingly, flow returns to S230 and continues as described above. In particular, additional parameter values for the MR scan are determined at S230 based on the current set of user-specified parameter values. The one or more determined additional parameter values are presented at S240, for example as shown in dialog 800 of FIG. 8. S240 may also include presentation of user interface 900 of FIG. 9 after receiving user selection of "OK" control of dialog 800.

Figure 10:
FIG. 10 is an outward view of a user interface for specifying scan parameters according to some embodiments.
Figure 11:
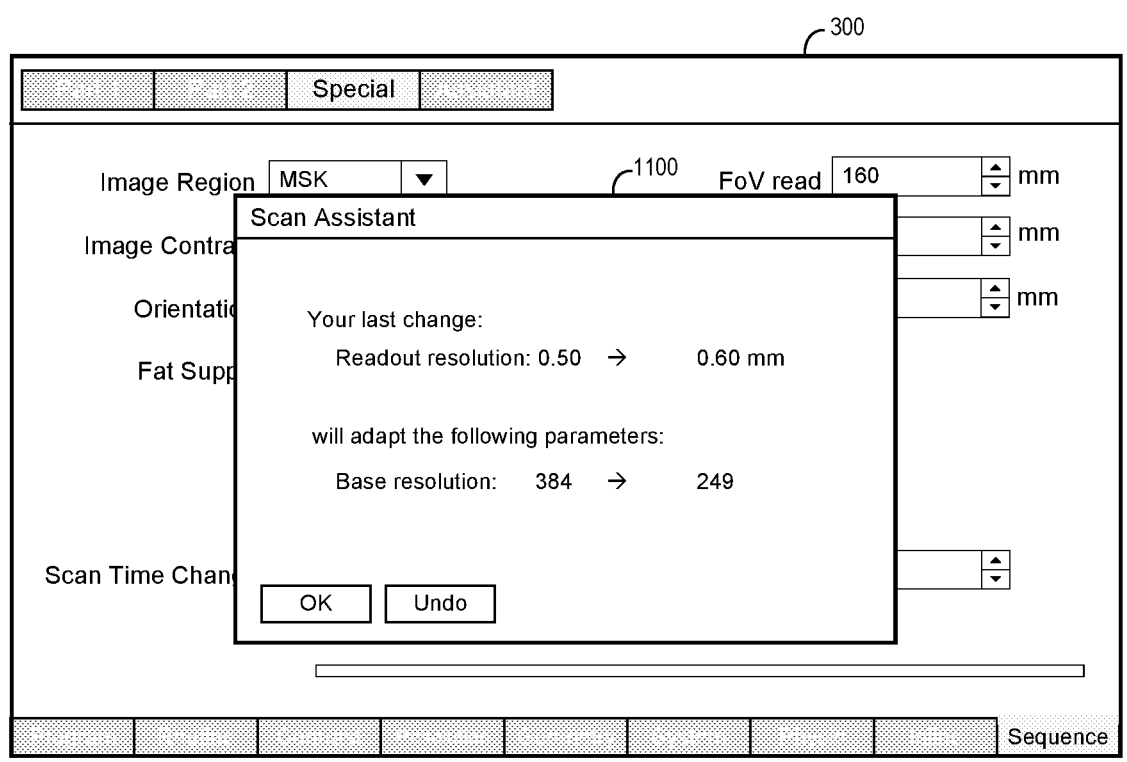
FIG. 11 is an outward view of a user interface for presenting scan parameter changes determined according to some embodiments.

FIG. 10 illustrates another example in which it is determined that the user has changed a parameter value of the MR scan. Specifically, the user has changed the value of the Readout Resolution parameter from "0.50" (as shown in FIG. 7) to "0.60". Accordingly, additional parameter values for the MR scan are determined at S230 based on the now-current set of user-specified parameter values (i.e., including Image Contrast=PD and Readout Resolution=0.60). Dialog 1100 of FIG. 11 presents, at S240, an additional parameter value determined at S230 which differs from the previously-determined value for the parameter.

Once the parameter values are as intended by the user, flow proceeds from S250 to S260. At S260, an MR scan is executed based on the current parameter values. According to some embodiments, one or more processing units 21 of system 20 may execute control program 23 to provide instructions to sequence controller 10 via MR system interface 24 based on the parameter values.

Various specific examples of and considerations for the determination of parameter values at S230 will now be described in further detail.

Some embodiments provide a reduced-sized parameter set from which a full MR scan parameter set will be derived. Values for the parameters of the reduced-sized parameter set may be efficiently determined by a clinician both because of the set's limited size and because the reduced-sized parameter set includes parameters with which a clinician is likely familiar. Moreover, the reduced-sized parameter set is selected such that an effective and suitable full MR scan parameter set may be derived therefrom. According to some embodiments, the reduced parameter set includes clinically-oriented parameters, such as but not limited to image region (e.g., Head, Knee, Liver, etc.), MR contrast type (e.g., T1, T2, PD, etc.), fat suppression (i.e., on or off), field-of-view (i.e., the extent of the anatomy to be visualized, in-plane and through-plane), resolution (i.e., desired spatial resolution) and slice thickness (i.e., resolution in the through-plane direction).

Some embodiments combine specified values of these parameters with information about the MR system and the patient setup, such as magnetic field strength, gradient field strength of the scanner, the transmitter and receiver configuration on the scanner, patient weight, patient positioning, and prior knowledge from previous localizer scans and system adjustment scans, to determine a full set of parameter values. Some embodiments suggest an optimal range of values for some parameters to accommodate personal preferences.

In a specific example, it will be assumed that a user inputs the following parameter values: Region=Knee, Contrast=T1, Fatsat=Yes, FOV=150 mm, Resolution=0.5 mm, Slices=35, Slice thickness=5 mm. In response, at S230, an appropriate MR pulse sequence is chosen, and information regarding the MR scanner is determined. Such information may include the magnetic field strength of the MR scanner, gradient system specifications, transmit and receive coil configuration, and other settings such as shims, frequencies, B0 maps, B1 maps, etc.

The FOV and slices may be determined from the input, or determination thereof may be automated based on images from a localizer scan. Depending on the field strength and the user-inputted values, the sequence locks a range of TR which would provide a T1 contrast at the field strength, for example, a range of 500-700 ms. The user may, in some embodiments override this suggestion and input a different number.

The echo train length of a turbo spin echo (TSE) is determined based on the region and desired contrast. In this example, an echo train length of 5 is chosen, with an allowed range of 5-11. The readout bandwidth is determined based on the field strength, gradient strength, resolution, region, receive coil, and contrast. In this case, a readout bandwidth of 210 Hz/pixel may be suggested.

The FOV and desired resolution will be used to determine the matrix size. In this example, with an FOV=150 and resolution=0.5, the determined matrix size is 300. Based on the field strength, imaging region, receive coil, other protocol parameters (e.g., a coil location, localizer scan or normalization scan), the maximum possible practically-achievable resolution (i.e., smallest pixel size and slice thickness) will be determined.

Whether or not to employ fat suppression is determined based on field strength, region, and any fat suppression RF pulse parameters coded in the chosen MR pulse sequence. In this specific example, a spectral adiabatic inversion pulse optimized for knee imaging is used. An optimal acceleration factor with a maximum acceleration factor may also be determined based on field strength, coil information, patient setup, noise estimates, coil locations, etc.

The following description provides general considerations which may be taken into account during the determination of S230 according to some embodiments.

Repetition time, (TR), echo time (TE), and turbo factor/echo train length (ETL) may be constrained based on user-specified image region and image contrast values. FOV, number of slices, matrix size, slice thickness, readout bandwidth, and RF pulse type may also be determined based on a specified image region. Concatenations may be modified to achieve desired TR depending upon image contrast values.

Parameter values may be generally determined to achieve a minimal scan time while maintaining resolution, number of slices, image contrast, and image quality requirements. Readout bandwidth may be determined based on specified image region and fat saturation preference. Phase encoding direction and phase-oversampling, flow-compensation, and saturation bands may be automatically determined based on image region and orientation identified from localizer images, and matrix size may be automatically determined based on resolution and FOV. Moreover, distortion correction, table position, $B_1$ and $B_0$ shim setting, pre-scan normalization, and imaging filter sets may be determined in view of obtaining optimal image quality and appearance.

The foregoing diagrams represent logical architectures for describing processes according to some embodiments, and actual implementations may include more or different components arranged in other manners. Other topologies may be used in conjunction with other embodiments. Moreover, each component or device described herein may be implemented by any number of devices in communication via any number of other public and/or private networks. Two or more of such computing devices may be located remote from one another and may communicate with one another via any known manner of network(s) and/or a dedicated connection. Each component or device may comprise any number of hardware and/or software elements suitable to provide the functions described herein as well as any other functions. For example, any computing device used in an implementation of a system according to some embodiments may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Flash drive, magnetic tape, and solid state Random Access Memory (RAM) or Read Only Memory (ROM) storage units. Embodiments are therefore not limited to any specific combination of hardware and software.

Embodiments described herein are solely for the purpose of illustration. Those in the art will recognize other embodiments may be practiced with modifications and alterations to that described above.

What is claimed is:

1. A system comprising:
a display;
a memory storing processor-executable process steps; and
a processor to execute the processor-executable process steps to cause the system to:
output a user interface on the display which is configured to receive parameter values for a reduced set of magnetic resonance (MR) scan parameters of a magnetic resonance scan from among a full set of MR scan parameters;
receive input parameter values for scan parameters included in the reduced set of MR scan parameters including values for of the magnetic resonance scan input via the displayed user interface;
automatically generate scan parameter values for magnetic strength and transmit/receive coil configurations of an MR system which are part of a full set of MR scan parameters based on the received input parameter values and field strength information of the MR system;
modify, via a first modification process, a previously stored parameter value for a scan parameter from the full set of MR scan parameters for the magnetic resonance scan which is not visible on the user interface based on the input parameter value of the scan parameter included in the reduced set of MR scan parameters, receive coil configuration of a respective MR system that is to perform the MR scan, and a patient setup at the respective MR system;
output a descriptive notification via a dialog interface on the display which makes visible the previously stored parameter value for the scan parameter from the full set of MR scan parameters and describes how the previously stored parameter value has been modified,
determine whether a user has changed an input parameter value of an additional MR scan parameter from the reduced set of parameter values after the output;
in response to determining the user has changed the input parameter value of the additional MR scan parameter, modify, via a second modification process, a previously stored parameter value for a different scan parameter from the full set of MR scan parameters which is not included within the reduced set of MR scan parameters, which is not changed during the first modification process, and which is not visible on the user interface, and output a second descriptive notification via the dialog interface which describes how the previously stored parameter value of the different scan parameter has been modified; and
execute a scan operation based on the full set of MR scan parameters modified via the first and second modification processes.

2. The system according to claim 1, wherein the reduced set of MR scan parameters comprise predetermined MR scan parameters from which the full set of MR scan parameters can be derived.

3. The system according to claim 1, wherein the input parameter values for the reduced set of MR scan parameters are the only MR scan parameters which can be input via the user interface.

4. The system according to claim 1, the processor to further execute the processor-executable process steps to cause the system to:
receive a second set of input parameter values for the magnetic resonance scan via the displayed user interface; and
automatically determine an additional remaining value for the full set of MR scan parameters for the magnetic resonance scan based on the second set of input parameters.

5. The system according to claim 1, further comprising:
a chassis defining a bore;
a main magnet to generate a polarizing magnetic field within the bore;
a gradient system to apply a gradient magnetic field to the polarizing magnetic field; and a radio frequency system to transmit RF pulses to patient tissue disposed within the bore and to receive signals from the patient tissue, wherein the processor is to further execute the processor-executable process steps to cause the system to:

execute the magnetic resonance scan based on the input parameter values and the automatically determined at least one remaining value.

6. The system according to claim 1, wherein the processor is configured to automatically determine a plurality of values for a plurality of respective scan parameters which are not visible in the user interface and which combine with the input parameter values to generate a complete set of magnetic resonance scan parameters for a magnetic resonance scanning system.

7. The system of claim 1, wherein the at least one value for the full set of MR scan parameters is further determined based on one or more of a magnetic field strength of a scanner and a gradient field strength of the scanner.

8. The system of claim 1, wherein the receive coil configuration of the respective MR system comprises receive coil locations on the MR system.

9. A computer-implemented method comprising:

outputting a user interface on a display which is configured to receive parameter values for a reduced set of magnetic resonance (MR) scan parameters of a magnetic resonance scan from among a full set of MR scan parameters;

receiving an input parameter value for a scan parameter included in the reduced set of MR scan parameters of the magnetic resonance scan input via the displayed user interface;

automatically generating scan parameter values for magnetic field strength and magnetic field mappings of an MR system which are part of a full set of MR scan parameters based on the received input parameter values and field strength information of the MR system;

modifying, via a first modification process, a previously stored parameter value for a scan parameter from the full set of MR scan parameters for the magnetic resonance scan which is not visible on the user interface based on the input parameter value of the scan parameter included in the reduced set of MR scan parameters, receive coil configuration of a respective MR system that is to perform the MR scan, and a patient setup at the respective MR system;

outputting a descriptive notification via a dialog interface on the display which makes visible the previously stored parameter value for the scan parameter from the full set of scan parameters and describes how the previously stored parameter value has been modified;

determining whether a user has changed an input parameter value of an additional MR scan parameter from the reduced set of parameter values after the output;

in response to determining the user has changed the input parameter value of the additional MR scan parameter, modifying, via a second modification process, a previously stored parameter value for a different scan parameter from the full set of MR scan parameters which is not included within the reduced set of MR scan parameters, which is not changed during the first modification process, and which is not visible on the user interface, and outputting a second descriptive notification via the dialog interface which describes how the previously stored parameter value of the different scan parameter has been modified; and executing a scan operation based on the full set of MR scan parameters modified via the first and second modification processes.

10. The method according to claim 9, wherein the reduced set of MR scan parameters comprise predetermined MR scan parameters from which the full set of MR scan parameters can be derived.

11. The method according to claim 9, wherein the input parameter values for the reduced set of MR scan parameters are the only MR scan parameters which can be input via the user interface.

12. The method according to claim 9, wherein the automatically determining comprises automatically determining a plurality of values for a plurality of respective scan parameters which are not visible in the user interface and which combine with the input parameter values to generate a complete set of magnetic resonance scan parameters for a magnetic resonance scanning system.

13. The method according to claim 9, further comprising:

receiving a second set of input parameter values for the magnetic resonance scan via the displayed user interface; and automatically determining an additional remaining value for the full set of MR scan parameters for the magnetic resonance scan based on the second set of input parameters.

14. The method according to claim 9, further comprising:

executing the magnetic resonance scan based on the input parameter values and the automatically determined at least one remaining value.

15. A non-transitory computer-readable medium storing program code, the program code executable by a computer system to cause the computer system to:

output a user interface on a display which is configured to receive parameter values for a reduced set of magnetic resonance (MR) scan parameters of a magnetic resonance scan from among a full set of MR scan parameters;

receive an input parameter value for a scan parameter that is included in the reduced set of MR scan parameters of the magnetic resonance scan input via the displayed user interface;

automatically generate scan parameter values for magnetic field strength and magnetic field mappings of an MR system which are part of a full set of MR scan parameters based on the received input parameter values and field strength information of the MR system;

modify, via a first modification process, a previously stored parameter value for a scan parameter from the full set of MR scan parameters for the magnetic resonance scan which is not visible on the user interface based on the input parameter value of the scan parameter included in the reduced set of MR scan parameters, receive coil configuration of a respective MR system that is to perform the MR scan, and a patient setup at the respective MR system;

output a descriptive notification via a dialog interface on the display which makes visible the previously stored parameter value for the scan parameter from the full set of MR scan parameters and describes how the previously stored parameter value has been modified;

determining whether a user has changed an input parameter value of an additional MR scan parameter from the reduced set of parameter values after the output, in response to determining the user has changed the input parameter value of the additional MR scan parameter, modify, via a second modification process, a previously stored parameter value for a different scan parameter from the full set of MR scan parameters which is not included within the reduced set of MR scan parameters, which is not changed during the first modification process, and which is not visible on the user interface, and output a second descriptive notification via the dialog interface which describes how the previously stored parameter value of the different scan parameter has been modified; and execute a scan operation based on the full set of MR scan parameters modified via the first and second modification processes.

16. The medium according to claim 15, wherein the reduced set of MR scan parameters comprise predetermined MR scan parameters from which the full set of MR scan parameters can be derived.

17. The medium according to claim 15, wherein the input parameter values for the reduced set of MR scan parameters are the only MR scan parameters which can be input via the user interface.

18. The medium according to claim 15, the program code further executable by a computer system to cause the computer system to:

receive a second set of input parameter values for the magnetic resonance scan via the displayed user interface; and automatically determine an additional remaining value for the full set of MR scan parameters for the magnetic resonance scan based on the second set of input parameters.

19. The medium according to claim 15, the program code further executable by a computer system to cause the computer system to:

execute the magnetic resonance scan based on the input parameter values and the automatically determined at least one remaining value.

* * * * *